(12) United States Patent
Kikuchi et al.

(10) Patent No.: US 6,399,110 B1
(45) Date of Patent: Jun. 4, 2002

(54) GLUCOSE-CONTAINING PREPARATION

(75) Inventors: Takumi Kikuchi; Kouichi Hirano, both of Shimizu (JP)

(73) Assignee: Shimizu Pharmaceutical Co., Ltd., Shimizu (JP)

( * ) Notice: Subject to any disclaimer, the term of this patent is extended or adjusted under 35 U.S.C. 154(b) by 0 days.

(21) Appl. No.: 09/485,300

(22) PCT Filed: Aug. 19, 1998

(86) PCT No.: PCT/JP98/03674

§ 371 (c)(1),
(2), (4) Date: Apr. 27, 2000

(87) PCT Pub. No.: WO99/09953

PCT Pub. Date: Mar. 4, 1999

(30) Foreign Application Priority Data

Aug. 22, 1997 (JP) .............................................. 9-240231

(51) Int. Cl.$^7$ ........................ A01N 59/00; A61B 19/00; B65D 25/08
(52) U.S. Cl. ........................ 424/717; 424/715; 424/665; 604/410; 604/408; 604/416; 206/219
(58) Field of Search ................................. 424/717, 715, 424/677; 604/410

(56) References Cited

U.S. PATENT DOCUMENTS

| 5,289,644 A | | 3/1994 | Driskill et al. .................. 36/14 |
| 5,296,242 A | * | 3/1994 | Zander ........................ 424/717 |
| 5,871,477 A | * | 2/1999 | Isono et al. .................. 604/410 |
| 6,020,007 A | * | 2/2000 | Veech ........................ 424/677 |

FOREIGN PATENT DOCUMENTS

| EP | WO 93/09820 | * | 5/1993 | ............ A61M/1/14 |
| EP | 0 564 672 | | 10/1993 | |
| JP | 5-105633 | | 4/1993 | |
| JP | 8-131542 | | 5/1996 | |
| WO | 93/19792 | | 10/1993 | |

* cited by examiner

*Primary Examiner*—Thurman K. Page
*Assistant Examiner*—Isis Ghali
(74) *Attorney, Agent, or Firm*—Crowell & Moring LLP

(57) ABSTRACT

A neutral glucose-containing preparation with excellent stability and a near physiological pH, as a transfusion preparation with minimal glucose degradation by-products and a greatly reduced formic acid content; specifically, a glucose-containing preparation comprising separately housed first and second solutions, the first and second solutions satisfying the following conditions:

(a) the first solution contains 2–50% glucose, and its pH is adjusted to 3–5 with an organic acid buffer solution;

(b) the second solution contains an alkalizing agent, and has a pH value of 8–13 as a pH adjustor for the first solution; and (c) the glucose concentration is 1–15% in the preparation solution obtained by mixing the first solution and second solution, and the pH of the solution is in a range of 6–8.

It is used particularly as a peritoneal perfusate, such as a perfusate for Continuous Ambulatory Peritoneal Dialysis (CAPD).

12 Claims, No Drawings

GLUCOSE-CONTAINING PREPARATION

TECHNICAL FIELD

The present invention relates to a glucose-containing preparation, and more specifically, it relates to a neutral glucose-containing preparation with a near physiological pH, and particularly to preparations for peritoneal perfusion, including perfusates for Continuous Ambulatory Peritoneal Dialysis (CAPD).

BACKGROUND ART

Peritoneal perfusates, represented by CAPD perfusates, are perfusates used for dialysis that is carried out in renal failure patients that have lost kidney function, for excretion of wastes through the peritoneum and for maintenance of the balance of a various body fluid components. Such perfusates contain electrolyte components such as sodium chloride, calcium chloride, magnesium chloride and the like and salts of lactic acid, acetic acid, carbonic acid, bicarbonic acid, citric acid, pyruvic acid and the like as alkalizing agents, while containing glucose as an osmotic substance to ensure ultrafiltration of the perfusate.

Incidentally, transfusion preparations containing glucose as an osmotic substance are associated with a number of pharmaceutical problems. For example, when a glucose-containing aqueous solution from neutral to basic pH is heated, the glucose in the aqueous solution is thermally denatured, causing caramelization and further promoting degradation of the glucose itself.

On the other hand, the pH of transfusion perfusate preparations must be a nearly physiological pH, i.e. a pH from neutral to basic. Formulation and heat sterilization of glucose-containing perfusate preparations prepared with such pH values promotes degradation of the glucose in the preparations and is undesirable in terms of stability of the perfusate preparations. These same problems are also inherent in preparations containing glucose polymers such as polyglycol.

In order to overcome these problems there have been proposed perfusates with a near physiological pH, prepared by using two different packages as perfusate preparations, one package filled with a glucose-containing aqueous solution under specific conditions and the other package filled with an aqueous solution of electrolyte components and the like, and these are heat sterilized and then mixed together at the time of use.

For example, in Japanese Patent Application Laid-open No. 3-195561 there is disclosed a glucose-containing solution for various transfusions, peritoneal dialysis fluids or blood preservation solutions, wherein a first solution containing glucose and a second solution containing a component that promotes thermal degradation of glucose are housed separately from each other and steam sterilized.

In Japanese Patent Public Inspection No. 7-500992 there is disclosed a separately packaged and sterilized peritoneal perfusate preparation, comprising a small aqueous amount of an aqueous solution containing glucose at a high concentration, and a glucose-free solution containing a large liquid amount of a salt or the like.

The glucose-containing perfusate preparations provided by these publications are either based on the concept of separating the thermal degradation-promoting components from the glucose solution during heat sterilization of the glucose-containing aqueous solution to avoid thermal degradation of the glucose, and filling them into a separate solution to avoid degradation of the glucose (Japanese Patent Application Laid-open No. 3-195561), or attempt to inhibit production of glucose degradation products by using a glucose-containing aqueous solution in a small liquid amount and at high concentration (Japanese Patent Public Inspection No. 7-500992).

However, since the separately housed glucose-containing aqueous solutions in the perfusate preparations provided by these publications have high pH values, it still cannot be said that they are satisfactory in terms of stability. That is, long-term storage presents the problem of gradual degradation of the glucose contained in the aqueous solution, shifting the glucose-containing aqueous solution to its stable pH range of 3–5, and causing the fluid property of the solution itself to undergo alteration toward the acidic end. Consequently, preparations that exhibit altered fluid properties with storage cannot be considered desirable products from the standpoint of stability.

In order to overcome these problems there has recently been proposed a solution set for formulation of peritoneal dialysis fluids (Japanese Patent Application Laid-open No. 8-131542) that comprises an aqueous solution at pH 4–5 containing glucose and containing no lactic acid ion, as a first solution, with a second solution containing sodium lactate, wherein after mixing the first and second solutions the glucose concentration of the solution is 5–50 g/L, and the pH is adjusted to be in the range of 6–7.3, and the volume ratio of the first and second solutions is 5:5–9:1.

The solution set described in this publication is characterized in that the glucose and the lactic acid ion are filled separately so that the lactic acid ion is not present with the glucose to be sterilized, in order to avoid promoting glucose degradation by lactic acid ion during the heat sterilization, while the pH is also low, and in that the volume ratio of the glucose-containing solution and the glucose-free solution, i.e. the volume of the glucose-containing solution, is increased. This solution set gives peritoneal dialysis fluids at near physiological pH even when the mixture is carried out after heat sterilization.

However, while the first solution in the solution set proposed by this publication is a glucose-containing aqueous solution with a pH in the acidic range (pH 4–5) in order to avoid thermal degradation of the glucose by heat sterilization, it cannot be said that degradation of the glucose in the first solution is completely prevented, and the result is therefore still unsatisfactory.

Incidentally, it is known that glucose-containing aqueous solutions in a pH range of neutral to basic have a poor stability since the glucose gradually undergoes degradation by heat or long-term storage, producing such degradation products as 5-hydroxymethylfurfuranol (5-HMF) and formic acid. In particular, formic acid which has a rather high acidity causes the fluid property of the solution itself to shift toward the stable acidic range of pH 3–5 with accumulating degradation products. Its toxicity is also a problem to be dealt with.

It has therefore been strongly desired to develop a pharmaceutically stable glucose-containing transfusion preparation that minimizes this degradation of glucose, and particularly the by-production of formic acid under long-term storage conditions.

DISCLOSURE OF THE INVENTION

It is an object of the present invention to overcome the aforementioned problems by providing a transfusion preparation that allows greater stabilization of glucose-containing aqueous solutions, and particularly a transfusion preparation with minimal by-products of glucose degradation and extremely low formic acid contents in neutral glucose-containing preparations at near physiological pH.

It is a related object of the present invention to provide a glucose-containing transfusion preparation for use as a peritoneal perfusate, such as a perfusate for Continuous Ambulatory Peritoneal Dialysis (CAPD).

As the means therefor, the present invention provides a glucose-containing preparation comprising separately housed first and second solutions, the first and second solutions satisfying the following conditions:

(a) the first solution contains 2–50% glucose, and its pH is adjusted to 3–5 with an organic acid buffer solution;

(b) the second solution contains an alkalizing agent, and has a pH value of 8–13 as a pH adjustor for the first solution; and (c) the glucose concentration is 1–15% in the preparation solution that is obtained by mixing the first solution and second solution, and the pH of the solution is in a range of 6–8.

According to a concrete embodiment of the invention, the organic acid buffer solution of the glucose-containing first solution in the glucose-containing preparation is a lactic acid buffer solution, acetic acid buffer solution, citric acid buffer solution or pyruvic acid buffer solution, and specifically, in the case of a lactic acid buffer solution the buffer solution contains sodium lactate and lactic acid, in the case of an acetic acid buffer solution the buffer solution contains sodium acetate and acetic acid, in the case of a citric acid buffer solution the buffer solution contains sodium citrate and citric acid, and in the case of a pyruvic acid buffer solution the buffer solution contains sodium pyruvate and pyruvic acid.

As a more concrete embodiment, the alkalizing agent in the second solution of the present invention is a salt of lactic acid, acetic acid, carbonic acid, bicarbonic acid, citric acid or pyruvic acid.

The present invention is also a glucose-containing preparation wherein the adjusting solution with a pH of 8–13 as the second solution is a sodium hydroxide aqueous solution, a sodium bicarbonate aqueous solution or a sodium carbonate aqueous solution.

As yet a further concrete embodiment of the glucose-containing preparation of the present invention, one or more electrolyte components from among chlorides such as sodium chloride, zinc chloride, magnesium chloride and potassium chloride, carbonic acid, and organic acid salts such as acetic acid, lactic acid and gluconic acid salts, is compounded with either or both the aforementioned first solution and second solution.

As a result of diligent research by the present inventors, it is newly discovered that the production of degradation products such as 5-HMF and formic acid by thermal degradation of glucose itself under heat sterilization or long-term storage conditions is suppressed in an aqueous solution, which has been adjusted to the stable acidic pH range of 3–5 with an organic acid buffer solution, containing glucose at a high concentration, and that the formic acid content thereof decreases with time.

Furthermore, as will be shown by the results of test examples provided below, the first solution containing a high concentration of glucose in the glucose-containing preparation of the present invention includes a buffer solution of an organic acid such as lactic acid which adjusts the pH of the solution and buffers the solution itself, thus inhibiting production of formic acid while also decreasing with time the content of the formic acid by-product, whereas the formic acid content of a non-pH adjusted glucose-containing aqueous solution increases with time.

Thus, while a glucose-containing aqueous solution with a non-adjusted pH exhibits progressive degradation of glucose in the solution and an increased formic acid content, which lowers the pH of the solution, the glucose-containing aqueous solution of the present invention has the pH of the solution adjusted with an organic acid buffer solution, and therefore exhibits no pH reduction and has a lower formic acid content.

Furthermore, investigation by the present inventors has confirmed that when such a glucose-containing aqueous solution is mixed with a pH-adjusting solution containing electrolyte components to make a neutral glucose-containing transfusion preparation with a near physiological pH, the stability is much more satisfactory than previously proposed transfusion preparations.

BEST MODE FOR CARRYING OUT THE INVENTION

The present invention has been completed based on these totally new investigative results, and the glucose-containing preparation provided by the present invention is thus partly characterized by comprising a first solution that contains glucose, the pH of the solution being adjusted to be in the range of 3–5 with an organic acid buffer solution.

As organic acid buffer solutions there are preferred lactic acid buffer solutions, acetic acid buffer solutions, citric acid buffer solutions and pyruvic acid buffer solutions, and specifically, lactic acid buffer solutions containing sodium lactate and lactic acid, acetic acid buffer solutions containing sodium acetate and acetic acid, citric acid buffer solutions containing citric acid and sodium citrate, and pyruvic acid buffer solutions, containing pyruvic acid and sodium pyruvate. Potassium salts and the like may also be used instead of organic acid sodium salts.

These organic acid buffer solutions adjust the pH of the glucose-containing aqueous solution to a stable pH range of 3–5, thus making it possible to avoid by-products of degradation of the glucose itself even upon heat sterilization, to provide a more excellent long-term stability than by simply housing the glucose solution and electrolyte solution separately.

On the other hand, the second solution in the glucose-containing transfusion preparation provided by the present invention contains an alkalizing agent, and the solution has a pH value of 8–13 as a pH adjustor for the first solution.

As pH adjustors there may be mentioned sodium hydroxide, sodium bicarbonate and sodium carbonate, among which sodium bicarbonate and sodium carbonate are preferably used to adjust the pH to the desired value.

As alkalizing agents there may be mentioned salts of lactic acid, acetic acid, carbonic acid, bicarbonic acid, citric acid and pyruvic acid, among which are preferred sodium lactate and sodium acetate, and particularly sodium lactate.

The glucose-containing preparation of the present invention has the first solution and second solution separately housed from each other, with a glucose concentration of 1–15% in the transfusion preparation solution actually obtained by mixing the first solution and second solution, and a solution pH in the range of 6–8, wherein the transfusion preparation is adjusted to have a total volume of about 500 to 5000 ml.

Consequently, the glucose concentration of the glucose-containing first solution is preferably a concentration of 2–50%, and the pH of the solution with this glucose concentration is adjusted to 3–5 with an organic acid buffer solution.

On the other hand, while the pH of the second solution as the pH adjustor for the first solution has a value of 8–13, it is necessary for the solution volume of the pH adjustor with respect to the first solution volume to be such that the pH of the glucose-containing transfusion preparation after mixture of both is in the physiologically neutral range of 6–8. Judging from the fact that the solution volume of the transfusion preparation provided by the present invention is normally a volume of from about 500 to 5000 ml as the total volume, it is preferred for them to be separately housed with the proportion of the volumes of the first solution and second solution such that the solution volume of the second solution is 1–9 with respect to 1 as the solution volume of the first solution, while it is particularly preferred for them to be separated housed with the solution volume of the second solution at 1–7 with respect to 1 as the solution volume of the first solution.

For example, for a 1000 ml preparation as the transfusion preparation, the glucose-containing solution as the first solution is at 125–400 ml while the pH adjustor as the second solution is at 875–600 ml, and they are separately housed in such a manner as to give a total volume of 1000 ml. If a different preparation volume is desired, the solutions may be separately housed with solution volumes for the first solution and second solution that are proportional to those given above.

The glucose-containing preparation comprising the first solution and second solution separately housed from each other, which is provided according to the invention, is a transfusion preparation such as a perfusate for CAPD, and therefore as a transfusion preparation it contains electrolyte components such as sodium chloride, calcium chloride and magnesium chloride. One or more of these electrolyte components may be combined with either or both of the first and second solutions.

However, when combining calcium as an electrolyte component, its addition to the second solution will result in reaction with the component added as the pH adjustor, forming an insoluble calcium salt, and therefore it is more preferably added to the first solution.

These electrolyte components may be added to a sodium ion concentration of 10–160 mEq/L, a calcium ion concentration of 0–5 mEq/L, a magnesium ion concentration of 0–5 mEq/L, a chlorine ion concentration of 10–160 mEq/L, a potassium ion concentration of 0–20 mEq/L and an alkalizing agent concentration of 10–60 mEq/L, in the transfusion preparation of the invention obtained by mixing the first solution and second solution.

The glucose-containing preparation of the present invention having this construction is preferably applied, among other uses, as a peritoneal perfusate for CAPD.

Consequently, a more concrete embodiment of the present invention is a perfusate preparation for CAPD comprising the aforementioned first solution and second solution, wherein the first and second solutions are housed separately from each other, the first solution contains 2–50% glucose and has its pH adjusted to 3–5 with a lactic acid buffer solution, the second solution contains sodium lactate as an alkalizing agent and has a pH value of 8–13 as a pH adjustor for the first solution, the glucose concentration of the preparation solution obtained upon mixing the first and second solution is 1–15%, and the pH of the solution is in the range of 6–8. In this case, it is particularly preferred for the added electrolytes to be combined in amounts as such for Na ion concentration: 125–150 mEq/L, K ion concentration: 0–5 mEq/L, Ca ion concentration: 0–5.0 mEq/L, Mg ion concentration: 0.5–3.0 mEq/L, chlorine ion concentration: 90–120 mEq/L, alkalizing agent: 30–60 mEq/L.

The glucose-containing preparation provided by the invention has the first solution and second solution separately housed from each other, and its embodiment may take a form of a sterilized set where both are filled into two independent packs provided with a linking section allowing sterile linkage, or it may be a sterilized device wherein the first solution and second solution are each filled into separate chambers of a vessel provided with two chambers isolated by a heat seal or a linking channel allowing passage when a partition is broken by external manipulation.

It will be appreciated that, so long as the preparation basically involves using a vessel well-known in the field, wherein two individual independent vessels are aseptically combined to make one transfusion preparation, any various different modifications thereof are possible without any restriction to the types described above.

EXAMPLES

The features of the glucose-containing preparation of the present invention will now be explained in further detail by way of the following concrete test examples and examples.

1. Test Example 1

Stability Test for Glucose-containing First Solution

A 10% aqueous glucose solution was used, and the pH of the solution was adjusted to about 4.5 with 0.3 mEq/L sodium lactate and 0.4 mEq/L lactic acid. A non-pH-adjusted 10% aqueous glucose solution was used as a test control solution, and both solutions were subjected to heat sterilization and the degradation products and pH changes of the aqueous glucose solutions were observed.

As degradation products from glucose, the 5-HMF product was measured by HPLC at a detection wavelength of 284 nm, while the formic acid product was measured by HPLC at a detection wavelength of 210 nm.

The pH changes and changes in degradation products are shown in Table 1.

TABLE 1

| | Stability test results | |
|---|---|---|
| | Glucose-containing first solution of the invention | Non-adjusted glucose-containing aqueous solution |
| pH value before heat sterilization | 4.5 | 5.94 |
| pH value after heat sterilization | 4.43 | 4.60 |
| 5-HMF | 3.73 ppm | 4.31 ppm |
| Formic acid | 0.018 w/v % | 0.021 w/v % |

As clearly shown by the results in this table, the glucose-containing aqueous solution as the first solution of the invention exhibited no change from the pH of 4.5 at the first stage, due to the sodium lactate (0.3 mEq/L) and lactic acid (0.4 mEq/L) as lactic acid buffer solutions, thus allowing suppressed production of 5-HMF, while the production of formic acid in the first stage of the degradation product was also suppressed.

2. Test Example 2

Preparation of First Solution and Second Solution and Mixing Test

Aqueous solutions of glucose at 6%, 10% and 16% as first solutions were prepared with pH values in the range of 3–5 with lactic acid buffer solutions (sodium lactate/lactic acid), according to the formulations listed in Table 2.

As the second solutions, there were prepared the second solutions listed in Table 2 as pH-adjusting solutions for the first solution, having pH from 8–13 and containing sodium lactate in an amount giving the prescribed total concentration of 40 mEq/L upon mixing.

As electrolyte components, sodium chloride and calcium chloride were added to the second solutions in prescribed amounts, while the test was conducted with and without addition of calcium chloride in prescribed amounts to the first solution.

3. Test Example 3

Titrable Acidity Test on First Solution (Glucose-containing Aqueous Solution)

Samples were prepared using a 10% aqueous solution of glucose as the first solution of the invention, with the pH adjusted to be in the range of 3–5 by adding a lactic acid buffer solution or acetic acid buffer solution to the aqueous solution as an organic acid buffer solution.

The following samples were prepared for use as the samples.

Sample No.1: 1.0 mEq/L sodium lactate and 0.3 mEq/L lactic acid: pH 4.38

TABLE 2

Results for preparation of first solution/preparation of second solution, and mixing test (transfusion preparations)

| | First solution (glucose-containing aqueous solution) | | | | Second solution (pH adjusting solution) | | | First solution + second solution |
|---|---|---|---|---|---|---|---|---|
| | | Organic acid buffer solution (mEq/L) | | | pH adjuster (mEq/L) | | | (transfusion preparation) |
| Solution ratio (first solution: second solution) | Glucose concentration (%) | Na lactate | Lactic acid | pH | $Na_2CO_3$ | $NaHCO_3$ | pH | pH |
| 1:3 | 6 | 0.3 | 1.0 | 3.70 | 0.3 | — | 9.62 | 7.21 |
| | | | 0.9 | 3.74 | | | 9.72 | 7.37 |
| | 10 | 0.3 | 1.0 | 3.68 | | | 9.62 | 7.22 |
| | | | 0.9 | 3.72 | | | 9.71 | 7.33 |
| | 16 | 0.2 | 0.7 | 3.75 | | | 9.63 | 8.15 |
| | | | 1.0 | 3.60 | | | 9.63 | 7.15 |
| | | 0.3 | 0.7 | 3.78 | | | 9.64 | 8.12 |
| | | | 1.0 | 3.65 | | | 9.63 | 7.15 |
| | | | 1.0 | 3.65 | | | 9.63 | 7.21 |
| | | | 0.9 | 3.69 | | | 9.72 | 7.28 |
| 1:3 | 16 | 0.3 | 0.8 | 3.56 | — | 1.0 | 8.32 | 6.81 |
| | | | | 3.56 | | 2.0 | 8.62 | 7.21 |
| | | | | 3.56 | | 3.0 | 8.73 | 7.53 |
| | | | | 3.58 | | 2.5 | 8.66 | 7.34 |
| | | | | 3.57 | | 3.0 | 8.54 | 7.36 |
| 2:3 | 16 | 0.3 | 0.6 | 3.83 | — | 3.8 | 8.41 | 7.30 |
| | | | 0.8 | 3.72 | | 3.8 | 8.42 | 7.18 |
| | | | 1.0 | 3.63 | | 3.8 | 8.42 | 7.05 |
| | | | 0.6 | 3.83 | | 4.0 | 8.53 | 7.39 |
| | | | 0.8 | 3.72 | | 4.0 | 8.50 | 7.25 |

The first solutions and second solutions obtained by preparation according to these formulations were used and combined together, with the first solution at 500 ml and the second solution at 1500 ml (first solution:second solution volume ratio=1:3), to prepare a transfusion preparation with a total volume of 2000 ml, and the changes in the pH value were observed.

They were also combined with the first solution at 800 ml and the second solution at 1200 ml (first solution:second solution volume ratio=2:3), to prepare a transfusion preparation with a total volume of 2000 ml, and the changes in the pH value were observed.

The results are shown in Table 2 as the pH values for first solution+second solution.

As clearly shown by the results in this table, the glucose-containing transfusion preparations of the invention obtained by mixing the first solutions and second solutions had pH values adjusted to near 7, which is a physiologically neutral range, and the stability of the transfusion preparations was also very satisfactory.

Sample No.2: 0.3 mEq/L sodium lactate and 1.0 mEq/L lactic acid: pH 3.62

Sample No.3: 1.0 mEq/L sodium acetate and 0.3 mEq/L acetic acid: pH 5.03

Sample No.4: 0.3 mEq/L sodium acetate and 1.0 mEq/L acetic acid: pH 4.22

Using 100 ml of each sample, titration was performed with an aqueous solution of 0.1 N sodium hydroxide (100 mEq/L), and the titrant at the point where the pH of the sample solution reached 7.4 was measured with an automatic titrator. The titrating solutions for each of the sample solutions were the following.

Sample No. Final pH Value/0.1 N Sodium Hydroxide Aqueous Solution

Sample No. 1: pH 7.55/0.32 mEq (0.32 ml/100 ml)
Sample No. 2: pH 7.41/0.087 mEq (0.87 ml/100 ml)
Sample No. 3: pH 7.51/0.045 mEq (0.45 ml/100 ml)
Sample No. 4: pH 7.39/0.104 mEq (1.04 ml/100 ml)

As clearly shown by these results, the glucose-containing aqueous solutions as the first solution of the invention had their pH values adjusted to 3–5 with a lactic acid buffer solution or acetic acid buffer solution as the organic acid buffer solution, but the pH values of these solutions could still be easily adjusted, judging from the titrable acidity. In particular, it is seen that when the first solution is used at 100 ml, the titration amount required to bring the pH to 7.4 with the 0.1 N sodium hydroxide aqueous solution is preferably no greater than 2 ml.

4. Test Example 4

Changes in Formic Acid Content in First Solution (Glucose-containing Aqueous Solution) upon Long-term Storage at High Temperature (1)

Using a 10% glucose-containing aqueous solution as the first solution of the invention, the pH of the solution was adjusted to about 3.5 with 0.3 mEq/L of sodium lactate and 0.8 mEq/L of lactic acid. As a control solution there was used a non-pH-adjusted 10% glucose-containing aqueous solution. Both of these were stored for 3 weeks in a chamber under conditions of 60° C. temperature, 30% humidity, and the change in the content of the formic acid degradation product in the solution with time was observed after 1 week, 2 weeks and 3 weeks.

The formic acid was assayed by HPLC at a detection wavelength of 210 nm.

The results are shown in Table 3.

TABLE 3

| Change in formic acid content with high-temperature storage (units: ppm) | | | |
|---|---|---|---|
| | After 1 week | After 2 weeks | After 3 weeks |
| Glucose-containing first solution of the invention (pH-adjusted) | 19 | 12 | 8 |
| Non-pH-adjusted control solution | 22 | 27 | 33 |

As clearly shown by the results in this table, the glucose-containing first solution of the invention exhibited a decrease in the formic acid degradation product of glucose with time, resulting from adjustment of the aqueous solution pH with the lactic acid buffer solution. In contrast, the non-pH-adjusted glucose-containing solution used as the control solution exhibited an increase in formic acid content with time.

5. Test Example 5

Changes in Formic Acid Content in First Solution (Glucose-containing Aqueous Solution) upon Long-term Storage at High Temperature (2)

Using a 7.72% glucose-containing aqueous solution as the first solution of the invention, the pH of the solution was adjusted to about 4.11 with 0.3 mEq/L of sodium lactate and 0.3 mEq/L of lactic acid. The solution was then stored in a chamber under conditions of 60° C. temperature and 30% humidity, and after 1, 2, 3, 4 and 6 weeks, the change in the content of the formic acid degradation product in the glucose-containing aqueous solution with time was measured in the same manner as Test Example 4 and observed.

The results are shown in Table 4.

TABLE 4

| Change in formic acid content with high-temperature storage (units: ppm) | | | | | |
|---|---|---|---|---|---|
| Immediately after preparation | After 1 week | After 2 weeks | After 3 weeks | After 4 weeks | After 6 weeks |
| Formic acid 74 | 30 | 25 | 21 | 15 | 15 |

As clearly shown by the results in this table, the glucose-containing first solution of the invention in this test example also exhibited a decrease in the content of the formic acid degradation product of glucose with time.

Judging from the results of the test examples given above, the glucose-containing first solutions in the glucose-containing preparations provided by the present invention, which contained an organic acid such as lactic acid to adjust the pH of the aqueous solutions for buffering, exhibited decreased formic acid contents with time, whereas the non-pH-adjusted glucose-containing aqueous solutions instead exhibited an increase in formic acid content with time.

In other words, the mechanism working in the glucose-containing aqueous solutions that remained without pH adjustment was progressive degradation of the glucose in the aqueous solutions, which resulted in increased formic acid contents and lowered the pH values of the solutions to stabilized ranges.

In contrast, with the glucose-containing aqueous solutions of the present invention, it is believed that the use of the organic acid buffering agents provided buffers in the solutions, while also pre-adjusting the pH values of the solutions to the stable range of 3–5, so that no further pH reduction was observed and the formic acid contents thus decreased with time.

Preparation Examples

As first solutions, there were prepared 500 ml glucose-containing aqueous solutions containing glucose at 6%, 10% and 16%, with 1.028 g of calcium chloride added thereto, and with the pH adjusted to 3–5 with lactic acid and sodium lactate.

As second solutions, there were prepared 1500 ml aqueous solutions to which there were added 11.95 g of sodium lactate, 0.68 g of magnesium chloride and 7.17 g of sodium chloride, with the pH adjusted to 8–13 with sodium carbonate or sodium bicarbonate.

These first and second solutions obtained above were separated independently from each other, housed in publicly known vessels with a linking section allowing aseptic linkage between them at the time of use, and were then heat sterilized to obtain glucose-containing preparations according to the present invention.

Industrial Applicability

According to the present invention, as explained above, a high-concentration glucose-containing solution with the pH adjusted to the stable acidic range of 3–5 with an organic acid buffer solution can avoid production of degradation products by heat degradation of glucose itself, under heat sterilization conditions or long-term storage conditions. In particular, it is possible to suppress production of the glucose degradation product, formic acid, and to reduce with time the amount of formic acid that is already produced, thus eliminating alteration of the solution by formic acid; hence, a glucose-containing preparation with very high pharmaceutical stability is provided.

The organic acid buffer solution used can also be appropriately selected as one having a titrable acidity that does not affect the pH upon mixing, and a neutral glucose-containing preparation brought to near physiological pH by mixture of this glucose-containing solution with an electrolyte component-containing pH adjusting solution exhibits highly satisfactory stability.

Consequently, the glucose-containing preparation of the present invention is excellent for use as a transfusion preparation, and particularly a CAPD peritoneal perfusate preparation, and is therefore of major value in medical care.

What is claimed is:

1. A glucose-containing preparation comprising separately housed first and second solutions, said first and second solutions satisfying the following conditions:
   (a) the first solution contains 2–50% glucose, and its pH is adjusted to 3–5 with an organic acid buffer solution;
   (b) the second solution contains an alkalizing agent, and has a pH value of 8–13 as a pH adjustor for said first solution; and
   (c) the glucose concentration is 1–15% in the preparation solution obtained by mixing the first solution and second solution, and the pH of the solution is in a range of 6–8.

2. The glucose-containing preparation according to claim 1, wherein the organic acid buffer solution of the first solution is a lactic acid buffer solution, acetic acid buffer solution, citric acid buffer solution or pyruvic acid buffer solution.

3. The glucose-containing preparation according to claim 2, wherein the lactic acid buffer solution is a buffer solution comprising sodium lactate and lactic acid, the acetic acid buffer solution is a buffer solution comprising sodium acetate and acetic acid, the citric acid buffer solution is a buffer solution comprising sodium citrate and citric acid, and the pyruvic acid buffer solution is a buffer solution comprising sodium pyruvate and pyruvic acid.

4. The glucose-containing preparation according to claim 1, wherein the alkalizing agent of the second solution is a salt of lactic acid, acetic acid, carbonic acid, bicarbonic acid, citric acid or pyruvic acid.

5. A glucose-containing preparation according to claim 1, wherein the adjusting solution with the pH of 8–13 in the second solution is an aqueous sodium hydroxide solution, an aqueous sodium bicarbonate solution or an aqueous sodium carbonate solution.

6. The glucose-containing preparation according to claim 1, wherein one or more electrolyte components are combined with either or both the first solution and second solution, 7. The glucose-containing preparation according to claim 1 which is a perfusate for Continuous Ambulatory Peritoneal Dialysis (CAPD).

8. A perfusate preparation for CAPD comprising separately housed first and second solutions, said first and said second solutions being such that the first solution contains 2–50% glucose and its pH is adjusted to 3–5 with a lactic acid buffer solution, the second solution contains sodium lactate as an alkalizing agent and has a pH value of 8–13 as a pH adjustor for said first solution, and the glucose concentration is 1–15% in the preparation solution obtained by mixing the first solution and second solution, the pH of the solution being in a range of 6–8

9. The glucose-containing preparation according to claim 2, wherein the organic acid buffer solution of the first solution is 1 mEq/L or less of a salt of the organic acid.

10. The glucose-containing preparation according to claim 1, wherein the alkalizing agent of the second solution is a salt of lactic acid.

11. The glucose-containing preparation according to claim 1, wherein the alkalizing agent of the second solution is a salt of citric acid.

12. The glucose-containing preparation according to claim 6, wherein said electrolyte components are selected from the group consisting of sodium chloride, calcium chloride, magnesium chloride and potassium chloride.

* * * * *